(12) United States Patent
Asano et al.

(10) Patent No.: US 9,695,460 B2
(45) Date of Patent: Jul. 4, 2017

(54) METHOD OF ANALYZING L-TRYPTOPHAN IN BIOLOGICAL SAMPLES, AND KIT USED THEREIN

(71) Applicants: Toyama Prefecture, Toyama (JP); Ajinomoto Co., Inc., Tokyo (JP)

(72) Inventors: Yasuhisa Asano, Toyama (JP); Masafumi Kameya, Toyama (JP); Hiroyasu Onaka, Toyama (JP)

(73) Assignees: Public University Corporation Toyama Prefectural University, Toyama (JP); Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 14/016,408

(22) Filed: Sep. 3, 2013

(65) Prior Publication Data

US 2013/0344526 A1    Dec. 26, 2013

Related U.S. Application Data

(63) Continuation of application No. PCT/JP2012/055386, filed on Mar. 2, 2012.

(30) Foreign Application Priority Data

Mar. 4, 2011 (JP) .................................. 2011-048101

(51) Int. Cl.
*C12Q 1/26* (2006.01)
(52) U.S. Cl.
CPC .............. *C12Q 1/26* (2013.01); *C12Y 104/03* (2013.01)
(58) Field of Classification Search
CPC ................................. C12Y 104/03; C12Q 1/26
See application file for complete search history.

(56) References Cited

FOREIGN PATENT DOCUMENTS

JP        06-070798      3/1994
JP        2001-069974    3/2001

OTHER PUBLICATIONS

Onaka et al, Characterization of the Biosynthetic Gene Cluster of Rebeccamycin from Lechevalieria aerocolonigenes ATCC 39243. Biosci. Biotechnol. Biochem., 67 (1), 127-138, 2003.*
Asamizu et al, Direct formation of chromopyrrolic acid from indole-3-pyruvic acid by StaD, a novel hemoprotein in indolocarbazole biosynthesis. Tetrahedron Letters 47 (2006) 473-475.*
Sebek et al, Microbiological Method for the Determination of L-Tryptophan. Journal of Bacteriology, Oct. 1965 vol. 90, No. 4 p. 1026-31.*
Nishizawa et al, Molecular Analysis of the Rebeccamycin L-Amino Acid Oxidase from Lechevalieria aerocolonigenes ATCC 39243. Journal of Bacteriology, Mar. 2005, p. 2084-2092 vol. 187, No. 6 p. 2084-92.*
Balibar et al, In Vitro Biosynthesis of Violacein from L-Tryptophan by the Enzymes VioA-E from Chromobacterium Violaceum. Biochemistry 2006, 45, 15444-15457.*
Chang et al, Cloning and Characterization of an Environmental DNA-Derived Gene Cluster That Encodes the Biosynthesis of the Antitumor Substance BE-54017. J. Am. Chem. Soc. 2011, 133, 9996-9999.*
Balibar et al, Terrequinone a biosynthesis through L-tryptophan oxidation, dimerization and bisprenylation. Nature Chemical Biology vol. 3 No. 9 Sep. 2007 p. 584-92.*
Chang et al, Cloning and Characterization of an Environmental DNA-Derived Gene Cluster That Encodes the Biosynthesis of the Antitumor Substance BE-54017. J. Am. Chem. Soc., 2011, 133 (26), pp. 9996-9999.*
Registry of Standard Biological Parts, 2010. Assay of K274002 L-tryptophan oxidase activity.*
Registry of Standard Biological Parts K274002 L-tryptophan oxidase, Alignment with Seq ID No. 1.*
August et al, Sequence Analysis and Functional Characterization of the Violacein Biosynthetic Pathway from Chromobacterium violaceum. J. Mol. Microbiol. Biotechnol. (2000) 2(4): 513-519.*
NCBI Acc#AAD51808 from August et al, J. Mol. Microbiol. Biotechnol. (2000) 2(4): 513-519.*
Izidoro et al, Biochemical and functional characterization of an L-amino acid oxidase isolated from *Bothrops pirajai* snake venom. Bioorganic & Medicinal Chemistry 14 (2006) 7034-7043.*
Bender et al, The Oxidation of Various Synthetic a-Amino-acids by Mammalian D-Amino-acid Oxidase, L-Amino-acid Oxidase of Cobra Venom and the L- and D-Amino-acid Oxidases of Neurospora crassa. Biochem J. Feb. 1950; 46(2): 210-219.*
Kameya et al, Selective tryptophan determination using tryptophan oxidases involved in bis-indole antibiotic biosynthesis. Anal Biochem. Jul. 15, 2013;438(2):124-32. doi: 10.1016/j.ab.2013.03.024. Epub Mar. 29, 2013.*
Emanuele, J. J. et al., "Purification and Characterization of the Flavoprotein Tryptophan 2-Monooxygenase Expressed at High Levels in *Escherichia coli*," (1995) Arch Biochem Biophys 316,241-248.
Simonian, A. L. et al., "A tryptophan-2-monooxygenase based amperometric biosensor for L-tryptophan determination: use of a competitive inhibitor as a tool for selectivity increase," (1997) Biosensors & Bioelectronics 12, 363-371.

(Continued)

*Primary Examiner* — Sheridan Swope
(74) *Attorney, Agent, or Firm* — Shelly Guest Cermak; Cermak Nakajima & McGowan LLP

(57) ABSTRACT

Disclosed is a method for quantifying L-tryptophan involving a step for mixing a specimen, L-tryptophan oxidase, and water, a step for allowing the obtained reaction solution to stand a predetermined period of time in the presence of oxygen, and a step for measuring the reaction product resulting from action of enzymes present in the reaction solution after allowing to stand. Also disclosed are a kit used to quantify the L-tryptophan containing L-tryptophan oxidase, and an enzyme sensor using the L-tryptophan oxidase. This method, kit and enzyme sensor use an L-tryptophan-specific enzyme, so are capable of quantifying L-tryptophan even in the presence of other amino acids.

7 Claims, 5 Drawing Sheets

(56) References Cited

OTHER PUBLICATIONS

Balibar, C. J., et al., "In Vitro Biosynthesis of Violacein from L-Tryptophan by the Enzymes VioA-E from Chromobacterium violaceum," (2006) Biochemistry 45, 15444-15457.

Onaka H. et al., "Cloning of the Staurosporine Biosynthetic Gene Cluster from Streptomyces sp. TP-A0274 and Its Heterologous Expression in Streptomyces lividans," (2002) J Antibiot 55, 1063-1071.

Tönismägi, K. et al., "L-Amino acid oxidase from Vipera lebetina venom: Isolation, characterization, effects on platelets and bacteria," (2006) Toxicon 48, 227-237.

Tan, N. H. et al., "Substrate Specificity of King Cobra (Ophiophagus hannah) Venom L-Amino Acid Oxidase," (1991) Int J Biochem 23, 323-327.

Yang, H. et al., "Cloning, characterization and expression of escapin, a broadly antimicrobial FAD-containing L-amino acid oxidase from ink of the sea hare Aplysia californica," (2005) J Exp Biol 208,3609-3622.

Ehara, T. et al., "Antimicrobial action of achacin is mediated by L-amino acid oxidase activity," (2002) FEBS Lett 531, 509-512.

Geueke, B. et al., "A new bacterial L-amino acid oxidase with a broad substrate specificty: purification and characterization," (2002) Enzyme Microb Technol 31, 77-87.

Tong, H. et al., "SO-LAAO, a Novel L-Amino Acid Oxidase That Enables Streptococcus oligofermentans to Outcompete Streptococcus mutans by Generating H202 from Peptone," (2008) J Bacteriol 190, 4716-4721.

Onaka H. et al., "pTOYAMAcos, pTYM18, and pTYM19, Actinomycete-Escherichia coli Integrating Vectors for Heterologous Gene Expression," (2003) J Antibiot 56, 950-956.

August 'Full=Probable L-tryptophan oxidase VioA.' (Feb. 8, 2011), UniProtKB/Swiss-Prot: Q9S3V1.2.

Onaka 'L-amino acid oxidase' (Oct. 31, 2006), UniProtKB/Swiss-Prot: Q83WG4.

Kameya M., et al., "Development of Trp quantitative analysis using Trp oxidase derived from Bisindole antibiotics biosynthetic pathway," vol. 2011 p. 39 (Mar. 5, 2011) with its English excerpt.

International Search Report and Search Opinion issued in PCT/JP2012/055386 (Apr. 24, 2012).

Japanese version of International Preliminary Report on Patentability of Chapter I for PCT/JP2012/055386 (Sep. 10, 2013).

English version of International Preliminary Report on Patentability of Chapter I for PCT/JP20121055386 (Sep. 10, 2013).

Office Action from Chinese Patent App. No. 201280011699.0 (Jun. 18, 2015) with English translation thereof.

\* cited by examiner

METHOD OF ANALYZING L-TRYPTOPHAN IN BIOLOGICAL SAMPLES, AND KIT USED THEREIN

CROSS-REFERENCE TO RELATED APPLICATIONS

This application is a Continuation of, and claims priority under 35 U.S.C. §120 to, International Application No. PCT/JP2012/055386, filed Mar. 2, 2012, and claims priority therethrough under 35 U.S.C. §119 to Japanese Patent Application No. 2011-048101, filed Mar. 4, 2011, the entireties of which are incorporated by reference herein. Also, the Sequence Listing filed electronically herewith is hereby incorporated by reference (File name: 2013-09-03T_US-502_Seq_List; File size: 13 KB; Date recorded: Sep. 3, 2013).

BACKGROUND OF THE INVENTION

Field of the Invention

The present invention relates to a method for analyzing L-tryptophan employing L-tryptophan oxidase suited to measuring the content of L-tryptophan by converting the L-tryptophan in a biological sample into a product permitting the quantification of L-tryptophan and detecting or quantifying the product.

Brief Description of the Related Art

The quantification of amino acid concentrations in biological samples such as blood can be effective for detecting various diseases. The development of such quantification methods is highly desirable from a medical treatment perspective. Enzymatic methods of quantifying amino acid concentrations afford great advantages over instrumental analysis in terms of speed, convenience, and the like. They are considered useful for the detection of various illnesses at the actual medical treatment site.

Known prior art relating to the enzymatic quantification of L-tryptophan includes methods employing (i) L-tryptophan monooxygenase (Emanuele, J. J., Heasley, C. J., and Fitzpatrick, P. F. (1995) Arch Biochem Biophys 316, 241-248 and Simonian, A. L., Rainina, E. I., Fitzpatrick, P. F., and Wild, J. R. (1997) Biosens Bioelectron 12, 363-371) and (ii) methods employing L-amino acid oxidase (Japanese Un-examined patent publication No. 2001-069974).

SUMMARY OF THE INVENTION

In the above-cited methods employing L-tryptophan monooxygenase, it is necessary to detect the amount of oxygen reduction accompanying the oxidation of L-tryptophan. Thus, in principle, a complex apparatus is required (Simonian, A. L., Rainina, E. I., Fitzpatrick, P. F., and Wild, J. R. (1997) Biosens Bioelectron 12, 363-371). The above L-tryptophan monooxygenase exhibits high relative activity of 83% to L-phenylalanine and 42% to L-methionine for an L-tryptophan activity of 100% (Emanuele, J. J., Heasley, C. J., and Fitzpatrick, P. F. (1995) Arch Biochem Biophys 316, 241-248). Thus, methods employing this enzyme are not suitable for convenient, low-cost, and highly L-tryptophan-specific detection.

In the above methods, employing L-amino acid oxidase, known L-amino acid oxidase generally has low substrate specificity and employs multiple L-amino acids other than L-tryptophan as a reaction substrate. Thus, there are no known examples of L-tryptophan-specific detection with L-amino acid oxidase in the presence of foreign substances. For example, multiple enzymes in snake venom are known as L-amino acid oxidases. However, all of these enzymes have activity for a broad range of amino acids (Tonismagi, K., Samel, M., Trummal, K., Ronnholm, G., Siigur, J., Kalkkinen, N., and Siigur, E. (2006) Toxicon 48, 227-237 and Tan, N. H., and Saifuddin, M. N. (1991) Int J Biochem 23, 323-327). In addition to these, there are also examples of reports of L-amino acid oxidases derived from mollusks and bacteria. However, these are similarly known to have broad substrate specificity (Yang, H., Johnson, P. M., Ko, K. C., Kamio, M., Germann, M. W., Derby, C. D., and Tai, P. C. (2005) J Exp Biol 208, 3609-3622, Ehara, T., Kitajima, S., Kanzawa, N., Tamiya, T., and Tsuchiya, T. (2002) FEBS Lett 531, 509-512, Geueke, B., and Hummel, W. (2002) Enzyme Microb Technol 31, 77-87, and Tong, H., Chen, W., Shi, W., Qi, F., and Dong, X. (2008) J Bacteriol 190, 4716-4721). In principle, it is impossible to use these enzymes to quantify L-tryptophan.

As enzymes with relatively high substrate specificity for L-tryptophan, there are examples of reports of L-amino acid oxygenase derived from a basidiomycete, *Coprinus* sp. (Japanese Un-examined patent publication No. 2001-069974). However, these enzymes also exhibit about 7% reactivity to other types of amino acids, such as L-phenylalanine. Accordingly, they are still unsuited to the detection of biological samples containing large amounts of foreign substances. The Km value of these enzymes for L-tryptophan is 650 µM, and the fact of low substrate affinity is problematic in the accurate quantification of L-tryptophan that is only present in concentrations on the order of several tens of µM in blood. As of the present, there are no known examples of the actual quantification of L-tryptophan in samples using L-amino acid oxygenase. Further, the genes of these enzymes have not yet been identified. Their manufacture entails the long-term (about a month) culturing of basidiomycetes and a complex purification process. For these reasons, the quantification of L-tryptophan in biological samples using these enzymes and practical applications requiring large quantities of these enzymes are hard.

Accordingly, an aspect of the present invention is to explore a new enzyme suitable for specifically quantifying L-tryptophan in biological samples in which other amino acids are also present, and to provide a new method for analyzing L-tryptophan using this enzyme.

A further aspect of the present invention is to provide a measuring kit that can be used when implementing the above enzymatic analysis method. A still further aspect of the present invention is to provide an enzyme sensor that can be used in the above enzymatic analysis method.

The present inventors discovered an L-tryptophan oxidase with high substrate specificity to L-tryptophan from a gene in the bis-indole antibiotic biosynthesis pathway of a bacterium. It was discovered that it was possible to produce detectable compounds by reacting this enzyme with L-tryptophan contained in a biological sample, and that this enzyme could specifically quantify L-tryptophan in biological samples without being affected by other amino acids also present. The present invention was devised on that basis.

The present invention is as follows:

It is an aspect of the present invention to provide a method for analyzing L-tryptophan in a specimen, comprising the steps of:

(A) mixing the specimen, L-tryptophan oxidase, and water, producing a reaction solution, (B) allowing the reaction solution to stand for a prescribed period in the presence of oxygen, producing at least one type of reaction product, and either (C) confirming the presence of the at least one type of reaction product due to the action of the L-tryptophan oxidase present in the reaction solution after standing for the prescribed period, or (D) measuring the quantity of the at least one type of the reaction product;

wherein the L-tryptophan oxidase comprises an amino acid sequence selected from the group consisting of:
  (a) the amino acid sequence of SEQ ID NO: 1 or 2,
  (b) a variant amino acid sequence comprising SEQ ID NO: 1 or 2 but which has 1 to 50 amino acid deletions, substitutions, and/or additions, and
  (c) an amino acid sequence having 90% or greater homology with the amino acid sequence of SEQ ID NO: 1 or 2, and
  wherein said L-tryptophan oxidase comprises:
  (i) oxidase activity on L-tryptophan in the presence of oxygen and water to produce hydrogen peroxide and ammonia,
  (ii) oxidase activity on L-phenylalanine falling within a range of 0 to 3% of the oxidase activity on L-tryptophan, and
  (iii) no oxidase activity on the protein-constituting amino acids other than L-tryptophan and L-phenylalanine It is a further aspect of the present invention to provide the method as described above, wherein the oxidase activity on L-phenylalanine falls within a range of 0 to 1% of the oxidase activity on L-tryptophan.

It is a further aspect of the present invention to provide the method as described above, wherein, prior to step (A), the L-tryptophan oxidase employed is stored in the presence of a stabilizing agent.

It is a further aspect of the present invention to provide the method as described above, wherein the stabilizing agent is selected from the group consisting of glycerol, sucrose, sorbitol, trehalose, can combinations thereof.

It is a further aspect of the present invention to provide the method as described above, wherein the reaction product is hydrogen peroxide.

It is a further aspect of the present invention to provide a kit for analyzing L-tryptophan comprising:
L-tryptophan oxidase,
wherein the L-tryptophan oxidase comprises an amino acid sequence selected from the group consisting of:
  (a) the amino acid sequence of SEQ ID NO: 1 or 2,
  (b) a variant amino acid sequence comprising SEQ ID NO: 1 or 2 but which has 1 to 50 amino acid deletions, substitutions, and/or additions, and
  (c) an amino acid sequence having 90% or greater homology with the amino acid sequence of SEQ ID NO: 1 or 2, and
  wherein said L-tryptophan oxidase comprises:
  (i) oxidase activity on L-tryptophan in the presence of oxygen and water to produce hydrogen peroxide and ammonia,
  (ii) oxidase activity on L-phenylalanine falling within a range of 0 to 3% of the oxidase activity on L-tryptophan, and
  (iii) no oxidase activity on the protein-constituting amino acids other than L-tryptophan and L-phenylalanine.

It is a further aspect of the present invention to provide the kit as described above, wherein the oxidase activity on L-phenylalanine falls within a range of 0 to 1% of the oxidase activity on L-tryptophan.

It is a further aspect of the present invention to provide the kit as described above, wherein the L-tryptophan oxidase is in a mixture with a stabilizing agent.

It is a further aspect of the present invention to provide the kit as described above, wherein the stabilizing agent is selected from the group consisting of glycerol, sucrose, sorbitol, trehalose, and combinations thereof.

It is a further aspect of the present invention to provide the kit as described above, further comprising a component selected from the group consisting of: a reaction buffer, a reagent for detecting hydrogen peroxide, an ammonia-detecting reagent, an indole pyruvic acid-detecting reagent, and combinations thereof.

It is a further aspect of the present invention to provide a composition for analyzing L-tryptophan comprising L-tryptophan oxidase,
wherein the L-tryptophan oxidase comprises an amino acid sequence selected from the group consisting of:
  (a) the amino acid sequence of SEQ ID NO: 1 or 2,
  (b) a variant amino acid sequence comprising SEQ ID NO: 1 or 2 but which has 1 to 50 amino acid deletions, substitutions, and/or additions, and
  (c) an amino acid sequence having 90% or greater homology with the amino acid sequence of SEQ ID NO: 1 or 2, and
  wherein said L-tryptophan oxidase comprises:
  (i) oxidase activity on L-tryptophan in the presence of oxygen and water to produce hydrogen peroxide and ammonia,
  (ii) oxidase activity on L-phenylalanine falling within a range of 0 to 3% of the oxidase activity on L-tryptophan, and
  (iii) no oxidase activity on the protein-constituting amino acids other than L-tryptophan and L-phenylalanine.

It is a further aspect of the present invention to provide a composition as described above, wherein the oxidase activity on L-phenylalanine falls within a range of 0 to 1% of the oxidase activity on L-tryptophan.

It is a further aspect of the present invention to provide a composition as described above, further comprising a stabilizing agent.

It is a further aspect of the present invention to provide a composition as described above, wherein the stabilizing agent is selected from the group consisting of glycerol, sucrose, sorbitol, trehalose, and combinations thereof.

It is a further aspect of the present invention to provide a sensor for detecting or quantifying L-tryptophan comprising L-tryptophan oxidase and an electrode, wherein the electrode detects hydrogen peroxide, and the L-tryptophan oxidase comprises an amino acid sequence selected from the group consisting of:
  (a) the amino acid sequence of SEQ ID NO: 1 or 2,
  (b) a variant amino acid sequence comprising SEQ ID NO: 1 or 2 but which has 1 to 50 amino acid deletions, substitutions, and/or additions, and
  (c) an amino acid sequence having 90% or greater homology with the amino acid sequence of SEQ ID NO: 1 or 2, and
  wherein said L-tryptophan oxidase comprises:
  (i) oxidase activity on L-tryptophan in the presence of oxygen and water to produce hydrogen peroxide and ammonia,
  (ii) oxidase activity on L-phenylalanine falling within a range of 0 to 3% of the oxidase activity on L-tryptophan, and
  (iii) no oxidase activity on the protein-constituting amino acids other than L-tryptophan and L-phenylalanine It is a further aspect of the present invention to provide the sensor as described above, wherein the oxidase activity on L-phenylalanine falls within a range of 0 to 1% of the oxidase activity on L-tryptophan.

It is a further aspect of the present invention to provide the sensor as described above, wherein the L-tryptophan oxidase is mixed with a stabilizing agent.

It is a further aspect of the present invention to provide the sensor as described above, wherein the stabilizing agent is selected from the group consisting of glycerol, sucrose, sorbitol, trehalose, and combinations thereof.

It is a further aspect of the present invention to provide the sensor as described above, wherein the electrode is an enzymatic hydrogen peroxide electrode or a membrane hydrogen peroxide electrode.

Effect of the Invention

The present invention permits rapid and convenient L-tryptophan-specific detection, even in samples containing large amounts of impurities such as other amino acids, by employing a tryptophan oxidase that is specific to L-tryptophan. In particular, the present invention is effective on biological samples such as plasma, blood serum, and urine, and quantification of L-tryptophan is possible by fluorescence methods and color-forming methods such as coupling with enzymes such as peroxidase, and an electrode-type enzyme sensor is provided as well.

DESCRIPTION OF THE PREFERRED EMBODIMENTS

<The Method for Analyzing L-Tryptophan>

Figure 1:
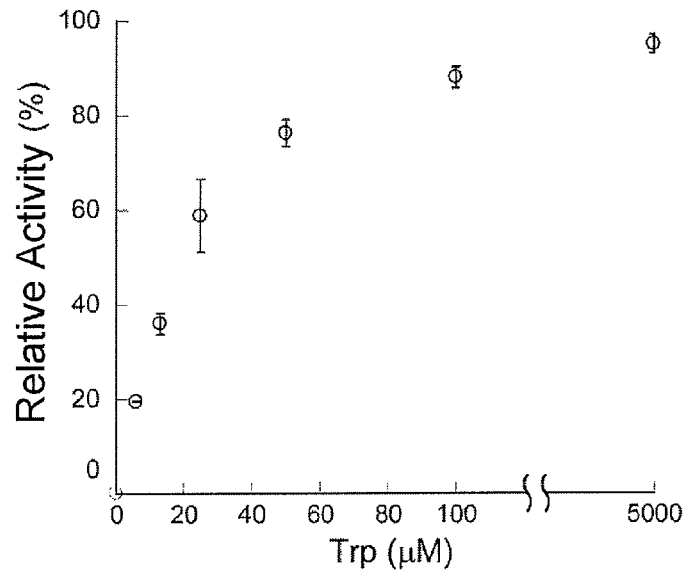
FIG. 1 shows StaO activity at various L-tryptophan concentrations.
Figure 2:
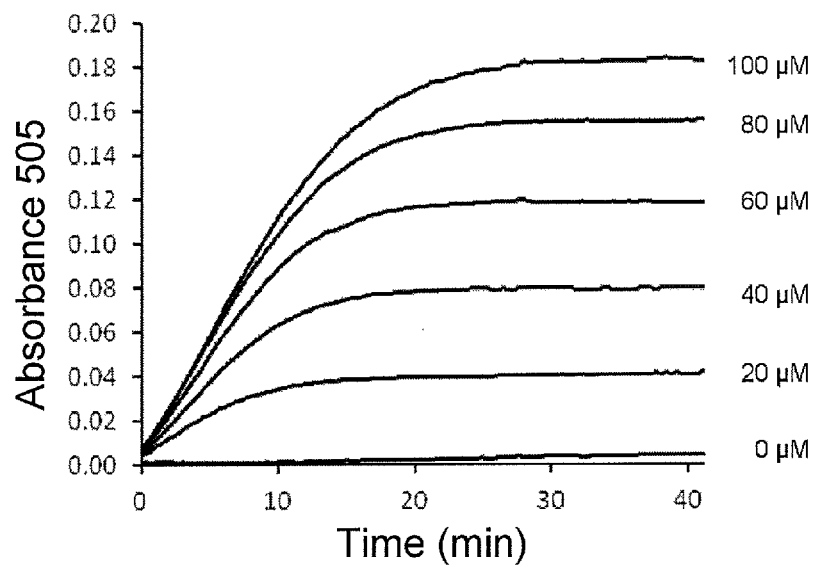
FIG. 2 shows the change over time in the absorbance of an L-tryptophan calibration curve generating sample with StaO.
Figure 3:
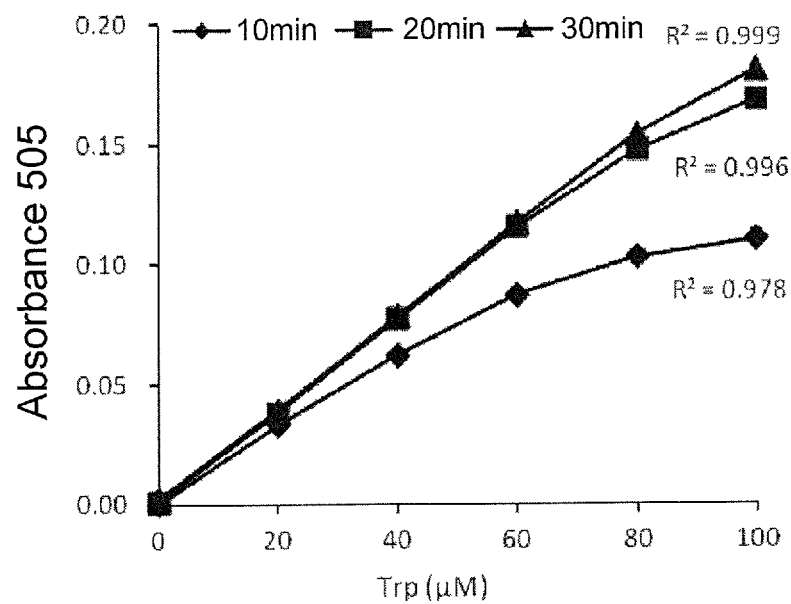
FIG. 3 shows L-tryptophan calibration curve generated with samples employing StaO.
Figure 4:
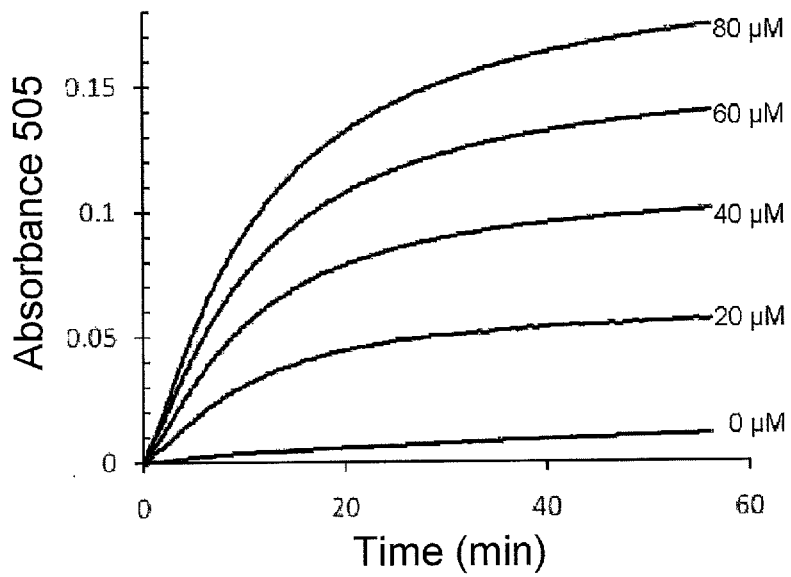
FIG. 4 shows the change over time in absorbance in samples used to generate L-tryptophan calibration curve with VioA.
Figure 5:
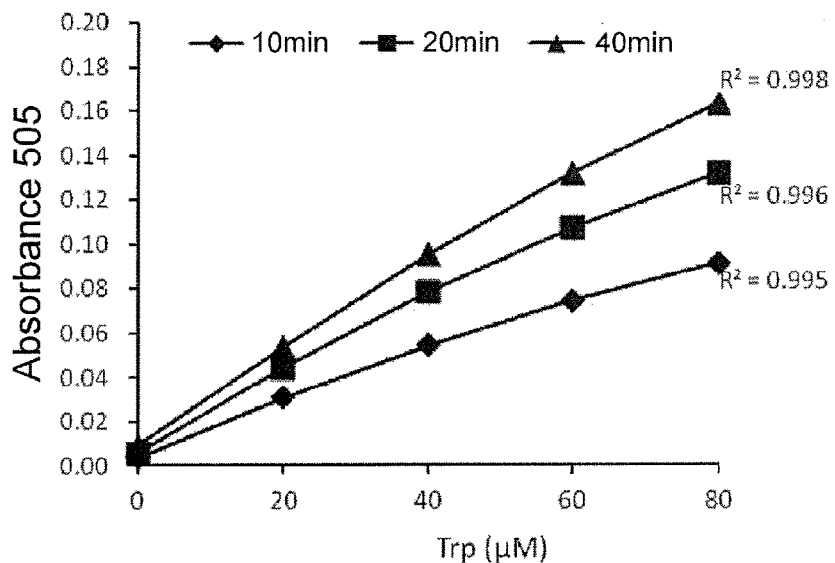
FIG. 5 shows an L-tryptophan calibration curve generated with samples employing VioA.

The method for analyzing L-tryptophan includes the steps of: (A) mixing a specimen, L-tryptophan oxidase, and water; (B) allowing the reaction solution obtained from said mixing to stand for a prescribed period in the presence of oxygen; and (C) confirming the presence of at least one type of reaction product due to the action of the enzyme present in the reaction solution after standing or measuring the quantity of at least one type of the reaction product. Through these steps, it is possible to confirm or quantify the presence of L-tryptophan in the specimen.

The specimen can be any biological sample potentially containing L-tryptophan. The biological sample can be suitably selected in view of what the product is that is produced by causing L-tryptophan oxidase to act on the biological sample and that is confirmed or quantified to confirm the presence of L-tryptophan, or measure the content thereof, in the biological sample. For example, when employing a color-forming agent or a fluorescent agent to confirm or quantify the product, a colorless aqueous solution is exemplary. Examples are blood serum and plasma.

The L-tryptophan oxidase can have an amino acid sequence of any one of (1) to (3) below (1) the amino acid sequence of SEQ ID NO: 1 or 2 in the Sequence Listing;

(2) an amino acid sequence of SEQ ID NO: 1 or 2 in the Sequence Listing with 1 to 50 amino acid deletions, substitutions, and/or additions, or (3) an amino acid sequence having 90% or greater homology with the amino acid sequence of SEQ ID NO: 1 or 2 in the Sequence Listing.

The L-tryptophan oxidase can have an oxidase activity which acts on L-tryptophan in the presence of oxygen and water to produce hydrogen peroxide and ammonia, or can have an oxidase activity on L-phenylalanine falling within a range of 0 to 3% of the oxidase activity on L-tryptophan. Also, the L-tryptophan oxidase can have no oxidase activity on the protein-constituting amino acids other than L-tryptophan and L-phenylalanine.

VioA is an enzyme that has the amino acid sequence given in SEQ ID NO: 1 in the Sequence Listing, that has oxidase activity of acting on L-tryptophan in the presence of oxygen and water to produce hydrogen peroxide and ammonia, oxidase activity on L-phenylalanine falling within a range of 0 to 3% of the oxidase activity on L-tryptophan, and that has no oxidase activity on the protein-constituting amino acids other than L-tryptophan and L-phenylalanine. VioA can be derived from *Chromobacterium violaceum*. VioA has been identified as an enzyme catalyzing part of the biosynthesis pathway of the antibiotic violacein that is produced by this bacterium and is reported to have L-tryptophan oxidation activity (Balibar, C. J., and Walsh, C. T. (2006) Biochemistry 45, 15444-15457). However, the enzymatic properties, such as the substrate specificity of the enzyme, have not yet been examined. Accordingly, the fact that VioA has oxidase activity of acting on L-tryptophan in the presence of oxygen and water to produce hydrogen peroxide and ammonia, has oxidase activity on L-phenylalanine falling within a range of 0 to 3% of the oxidase activity on L-tryptophan, and has no oxidase activity on protein-constituting amino acids other than L-tryptophan and L-phenylalanine are clarified for the first time as described herein. Furthermore, there has never been any report of the use of VioA to quantify L-tryptophan.

StaO is an enzyme that has the amino acid sequence given in SEQ ID NO: 2 in the Sequence Listing, that has oxidase activity of acting on L-tryptophan in the presence of oxygen and water to produce hydrogen peroxide and ammonia, that has oxidase activity on L-phenylalanine falling within a range of 0 to 3% of the oxidase activity on L-tryptophan, and that has no oxidase activity on the protein-constituting amino acids other than L-tryptophan and L-phenylalanine. StaO can be derived from *Streptomyces* sp. TA-A0724. The gene encoding StaO was discovered in the biosynthesis gene cluster of staurosporine, an antibiotic produced by the above bacterium (Onaka, H., Taniguchi, S., Igarashi, Y., and Furumai, T. (2002) J Antibiot 55, 1063-1071). This gene has no significant homology with the VioA gene, nor is there any example of biological analysis of the genetic product. Thus, the properties of the genetic product were unknown. Accordingly, the fact that StaO has oxidase activity of acting on L-tryptophan in the presence of oxygen and water to produce hydrogen peroxide and ammonia, has oxidase activity on L-phenylalanine falling within a range of 0 to 3% of the oxidase activity on L-tryptophan, and has no oxidase activity on the protein-constituting amino acids other than L-tryptophan and L-phenylalanine are clarified for the first time as described herein.

The phrase "oxidase activity on L-phenylalanine" and the "oxidase activity on L-tryptophan" in the phrase "oxidase activity on L-phenylalanine falling within a range of 0 to 3% of the oxidase activity on L-tryptophan" can mean the relative activity achieved when L-phenylalanine and L-tryptophan are employed, respectively, as the protein-constituting amino acid in the test method of "4. The substrate specificity on amino acids of L-tryptophan oxidase" in the Examples. The detection limits for all of the activity values obtained for the test method of "4. The substrate specificity on amino acids of L-tryptophan oxidase" are 0.5%. From the perspective of enhancing analysis precision, the oxidase activity on L-phenylalanine of the L-tryptophan oxidase can fall within a range of 0 to 2% of the oxidase activity on L-tryptophan, or within a range of 0 to 1.5%, or in another example, within a range of 0 to 1%.

Furthermore, the "oxidase activity on amino acids other than L-tryptophan and L-phenylalanine" in "has no oxidase activity on amino acids other than L-tryptophan and L-phenylalanine" can mean the relative activity achieved when employing amino acids other than L-tryptophan and L-phenylalanine as protein-constituting amino acids in the test method of "4. The substrate specificity on amino acids of L-tryptophan oxidase" in the Examples. Furthermore, the term "has no oxidase activity" or "no oxidase activity" can mean that the relative activity is 1% or less, or not exhibiting a relative activity exceeding the detection limit (0.5%).

The facts of having oxidase activity of acting on L-tryptophan to produce hydrogen peroxide and ammonia, an oxidase activity on L-phenylalanine falling within a range of 0 to 3% of the oxidase activity on L-tryptophan, and having no oxidase activity on the protein-constituting amino acids other than L-tryptophan and L-phenylalanine can be confirmed by use in analysis methods (quantification methods) described in the various Examples. The protein-constituting amino acids can refer to L-tyrosine, L-alanine, L-cysteine, L-aspartic acid, L-glutamic acid, L-glycine, L-histidine, L-isoleucine, L-lysine, L-leucine, L-methionine, L-asparagine, L-proline, L-glutamine, L-arginine, L-serine, L-threonine, and L-valine.

The range of "1 to 50" in the phrase "1 to 50 amino acid deletions, substitutions, and/or additions" can mean an enzyme in the form of a protein having such changes and the like which, in the presence of oxygen and water, has an oxidase activity of acting on L-tryptophan to produce hydrogen peroxide and ammonia; an oxidase activity on L-phenylalanine falling within a range of 0 to 3% the oxidase activity on L-tryptophan, and no oxidase activity on amino acids other than L-tryptophan and L-phenylalanine. From the perspective of a high ratio of the protein having oxidase activity, the above range of "1 to 50", can be, for example, 1 to 40, 1 to 30, 1 to 20, 1 to 10, 1 to 7, 1 to 5, or about 1 to 3.

The homology in the phrase "an amino acid sequence having 90% or greater homology with the amino acid sequence of SEQ ID NO: 1 or 2" is not specifically limited so long as the protein having the above amino acid sequence homology is an enzyme that has an oxidase activity of acting on L-tryptophan to produce hydrogen peroxide and ammonia in the presence of oxygen and water, that has an oxidase activity on L-phenylalanine falling within a range of 0 to 3% of the oxidase activity on L-tryptophan, and that has no oxidase activity on the amino acids other than L-tryptophan and L-phenylalanine. The homology of the amino acid sequence is not specifically limited other than that it be 90% or greater. However, it can be 95% or greater, 96% or greater, 97% or greater, 98%, or, 99% or greater.

The L-tryptophan oxidase can mean an enzyme, irrespective of the specific species from which it is manufactured, derived or purified, that produces hydrogen peroxide while specifically and oxidatively deaminating the amino group of L-tryptophan.

So long as the L-tryptophan oxidase has the same activity, it can include proteins and enzymes separated from the natural world, derived from living organisms, that are obtained by expressing the gene that encodes the enzyme in *E. coli*, or some other host in the form of a living organism.

As an example of a method of production by heterogeneous expression, the corresponding gene from genomic DNA that has been extracted from a biological species having the same activity is amplified by PCR, incorporated into pET, pUC, or the like to build a plasmid vector, and used to transform a host bacterium such as BL21 or JM109. The transformant is then cultured. Known methods other than this method can also be suitably employed.

The method of obtaining the L-tryptophan oxidase is not specifically limited; a protein synthesized by chemical synthesis and a recombinant protein fabricated by gene recombination technology are included. When fabricating a recombinant protein, the gene (DNA) coding for the corresponding protein can be obtained by a method set forth further below. By incorporating this DNA into a suitable expression system, it is possible to produce the above L-tryptophan oxidase.

The L-tryptophan oxidase can be prepared by a production method such as loading a gene coding for the above L-tryptophan oxidase onto a vector, transforming a host cell with the vector, culturing the host cell that has been transformed to accumulate the protein coding for the gene within the culture product, and collecting the accumulated protein.

The method of obtaining the gene coding for the L-tryptophan oxidase is not specifically limited. For example, the gene coding for the L-tryptophan oxidase can be fabricated by any method known to a person having ordinary skill in the art, such as chemical synthesis, genetic engineering methods, mutation induction, or the like based on information in the form of the amino acid sequence of SEQ ID NO: 1 or 2 or the base sequence given in SEQ ID NO: 3 or 4.

For example, the gene can be obtained by the method of bringing the DNA having the base sequence of SEQ ID NO: 3 or 4 in the Sequence Listing into contact with a reagent serving as a mutagen, the method of irradiation with UV radiation, and the method of genetic engineering. The site-specific mutation induction method, a method of genetic engineering, is a useful method in which a specific mutation is introduced at a specific position. The gene can be obtained by any known method.

Based on the information on the amino acid sequence given by SEQ ID NO: 1 or 2 or the base sequence given by SEQ ID NO: 3 or 4 in the Sequence Listing, suitable probes or primers can be prepared and then used to screen genome libraries of *Chromobacterium violaceum* NBRC 12614 or *Streptomyces* sp. TA-A0724 to isolate the gene. A genome library can be prepared by the usual methods from *Chromobacterium violaceum* NBRC 12614 or *Streptomyces* sp. TA-A0724.

The gene coding for the L-tryptophan oxidase can be obtained by the PCR method. PCR is conducted using a pair of primers designed to amplify the base sequence of SEQ ID NO: 3 or 4 using a genome library of *Chromobacterium violaceum* NBRC 12614 or *Streptomyces* sp. TA-A0724 as template. The PCR reaction conditions can be suitably established. For example, 30 cycles of a reaction cycle consisting of 30 seconds at 94° C. (denaturation), 30 second to 1 minute at 55° C. (annealing), and 2 minutes at 72° C. (elongation) can be conducted, after which a reaction can be conducted for 7 minutes at 72° C. Next, the amplified DNA fragment can be cloned into a suitable vector permitting amplification in a host such as *E. coli*.

Operations such as preparing the above probes or primers, constructing a genome library, screening a genome library, and cloning the target gene can be suitably carried out based on methods known to persons having ordinary skill in the art.

The above L-tryptophan oxidase gene can be inserted into a suitable vector for use. The type of vector is not specifically limited. For example, it can be an autonomously replicated vector (such as a plasmid), or one that is incorporated into the genome of a host cell during the course of introduction into the host cell, and replicated along with the chromosome into which it has been incorporated. The vector can be an expression vector. In an expression vector, the gene can be functionally linked to the elements required for transcription (such as promoters). A promoter is a DNA sequence that exhibits transcription activity in a host cell and can be suitably selected based on the type of host cell.

Examples of promoters that can function in bacteria cells are the *Geobacillus stearothermophilus* maltogenic amylase gene, *Bacillus licheniformis* alpha-amylase gene, *Bacillus amyloliquefaciens* BAN amylase gene, and *Bacillus subtilis* alkaline protease gene, as well as *Bacillus pumilus* xylosidase gene promoters, phage lambda $P_R$ and $P_L$ promoters, and *E. coli* lac, trp, and tac promoters.

Examples of promoters that can function in mammalian cells are the SV40 promoter, MT-1 (metallothionein gene) promoter, and adenovirus 2 major late promoter. Examples of promoters that can function in insect cells are the polyhedrin promoter, P10 promoter, *Autographa californica* polyhedrosis basic protein promoter, Baculovirus immediate early gene 1 promoter, and the Baculovirus 39K delayed-early gene promoter. Examples of promoters that can function in yeast host cells are promoters derived from yeast glycolytic system cells, alcohol dehydrogenase gene promoters, TPI1 promoter, and ADH2-4-c promoter. Examples of promoters that function in filamentous cells are ADH3 promoter and tpiA promoter.

As needed, the L-tryptophan oxidase gene can be functionally joined to a suitable terminator. The recombinant vector containing the L-tryptophan oxidase gene can also include elements such as polyadenylation signals (such as those derived from SV40 or the adenovirus 5E1b region) and transcription enhancer series (such as the SV40 enhancer). The recombinant vector containing the L-tryptophan oxidase gene can further include a DNA sequence permitting replication of the vector in a host cell, one example of which is the SV40 replication origin (when the host cell is a mammalian cell).

The recombinant vector containing the L-tryptophan oxidase gene can further include selection markers. Examples of selection markers are genes for which complements are lacking in the host cell, such as dihydrofolate reductase (DHFR) and the *Schizosaccharomyces pombe* TPI gene, and genes conferring resistance to drugs such as ampicillin, kanamycin, tetracycline, chloramphenicol, neomycin, and hygromycin. The methods used to splice the L-tryptophan oxidase gene, promoter, and, if necessary, terminator and/or secretion signal sequences and insert them into a suitable vector are known to persons having ordinary skill in the art.

The recombinant vector containing the L-tryptophan oxidase gene can be introduced into a suitable host to prepare a transformant. The host cell into which the recombinant vector containing the L-tryptophan oxidase gene is inserted can be any cell that is capable of expressing the L-tryptophan oxidase gene. Examples include bacteria, yeast, fungus, and higher eukaryotic cells.

Examples of bacterial cells include gram-positive cells such as *Bacillus* and *Streptomyces*, and gram-negative cells such as *E. coli*. These cells can be transformed by the protoplast method or by a known method employing a competent cell. Examples for mammalian cells include HEK293 cells, HeLa cells, COS cells, BHK cells, CHL cells, and CHO cells. Methods of transforming mammalian cells and inducing the expression of DNA sequences that have been introduced into the cells are also known. For example, the electroporation method, calcium phosphate method, and lipofection methods can be employed.

Examples of yeast cells include cells belonging to *Saccharomyces* or *Schizosaccaromyces*, such as *Saccharomyces cerevisiae* and *Saccharomyces kluyveri*. Examples of methods of introducing the recombinant vector into the host cell include the electroporation method, spheroblast method, and lithium acetate method.

Examples of fungus cells include filamentous bacteria such as cells belonging to *Aspergillus, Neurspora, Fusarium*, and *Trichoderma*. When employing a filamentous bacterium as a host cell, transformation can be conducted by incorporating the DNA construct into the host chromosome to obtain a recombinant host cell. The DNA construct can be introduced into the host chromosome by known methods, such as by homologous recombination or heterogenous recombination.

When employing an insect cell as the host cell, a vector into which the recombinant gene has been introduced and a Baculovirus can be jointly introduced into the insect cell with known methods to obtain a recombinant virus in the supernatant of an insect cell culture. The recombinant virus can then be used to infect insect cells and expression of the protein can be induced.

For example, the *Autographa californica* nuclear polyhedrosis virus, a virus infecting insects of the family *Mamestra brassicae*, can be employed as the Baculovirus.

Sf9 and Sf21, which are ovarian cells of *Spodoptera frugiperda* (Baculovirus Expression Vectors, A Laboratory Manual, W.H. Freeman and Company, New York (1992); HiFive (made by Initrogen)), which are Trichoplusiani ovarian cells, and the like can be employed as insect cells.

The calcium phosphate method and lipofection method are examples of methods of jointly introducing a recombinant gene introduction vector and Baculovirus into an insect cell to prepare a recombinant virus.

The above transformant can be cultured in a suitable culture medium under conditions permitting the expression of the gene that has been introduced. The usual protein isolation and purification methods can be employed to isolate and purify the L-tryptophan oxidase from the transformant culture. For example, when the L-tryptophan oxidase has been expressed in a dissolved state within the cell, culturing is terminated, the cells are recovered by centrifugal separation and suspended in an aqueous buffer, the cells are disrupted with an ultrasonic disruptor or the like, and a cell-free extract is obtained. The cell-free extract is centrifugally separated to obtain a supernatant, from which the L-tryptophan oxidase can be obtained as a purified product by the usual protein isolation and purification methods, employed singly or in combination. These methods include solvent extraction, salting out with ammonium sulfate, desalting, precipitation from an organic solvent, anion exchange chromatography employing a resin such as diethylaminoethyl (DEAE) Sepharose, cation exchange chromatography employing a resin such as S-Sepharose FF (made by Pharmacia), hydrophobic chromatography employing a resin such as Butyl-Sepharose or Phenyl-Sepharose, gel filtration employing a molecular sieve, affinity chromatography, chromatofocusing, and electrophoresis methods such as isoelectric electrophoresis.

The oxidation reaction of L-tryptophan by L-tryptophan oxidase is given by reaction formula A below:

Formula A

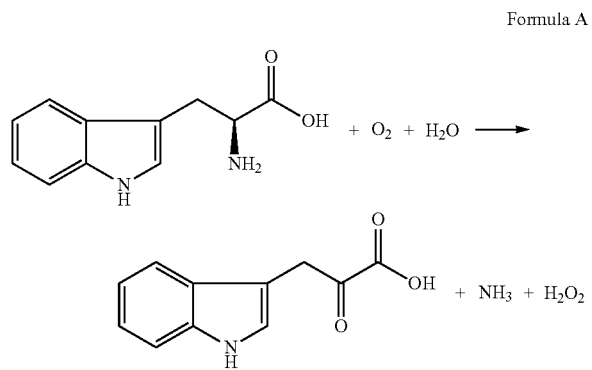

The L-tryptophan oxidase can mean an enzyme catalyzing the reaction given by Formula A above. Accordingly, it is not limited by differences in amino acid sequence or derivation.

Step (A)

It is suitable for the quantity of L-tryptophan oxidase that is admixed in step (A) to be 10 mU/mL or more (activity that consumes 1 μmol of tryptophan per minute is defined as 1 U). The quantity of water that is mixed in can be suitably determined based on the concentration of Trp in the sample or the total mass of the reaction system. For example, it can fall within a range of 5 to 95% of the total mass of the reaction system. As a molar ratio, it suffices for 1 mol or more of water to be present per mol of Trp, for example. When conducting the enzymatic reaction in an aqueous solution, the excess water will be present in the reaction system. There is no specific upper limit to the quantity of L-tryptophan oxidase that is admixed. In practical terms, it can be 100 mU/mL or lower, for example. However, there is no intent to limit to these ranges the quantity of L-tryptophan oxidase that is mixed in and the quantity of water that is mixed in, and they can be suitably adjusted.

In addition to L-tryptophan oxidase and water, a buffer solution exhibiting the optimum pH for L-tryptophan oxidase can be incorporated. When employing a buffer solution, water can be supplied as the buffer solution. It can also be incorporated as a stabilizing agent for L-tryptophan oxidase. The stabilizing agent of L-tryptophan oxidase can be, for example, at least one of glycerol, sucrose, sorbitol, and/or trehalose.

Step (B)

In step (B), the reaction solution that has been obtained by the above mixing is left standing for a prescribed period in the presence of oxygen.

In the L-tryptophan oxidation reaction by L-tryptophan oxidase, as indicated in reaction formula (A), an L-tryptophan deamination product in the form of indole-3-pyruvic acid, as well as ammonia ($NH_3$) and hydrogen peroxide ($H_2O_2$), are obtained as products. By conducting this reaction in contact with air, for example, the oxygen can be supplied in the form of dissolved oxygen in the reaction solution. There is normally no need to force feed an oxygen-containing gas such as air into the reaction solution to supply oxygen to the reaction solution. That is because only a trace amount of oxygen is required by the enzymatic reaction, which is amply provided by dissolved oxygen. The period for which the reaction solution is left standing for oxygen will depend on the quantity of enzyme employed. By way of example, it will fall within a range of from 10 minutes to one hour. However, there is no intent to limit it to this range, and it can be suitably adjusted.

Step (C)

In step (C), after standing, the presence of at least one species of reaction compound produced by the action of the enzyme that is present in the reaction solution is confirmed or the quantity of at least one species of reaction product is measured.

When the product the presence of which is confirmed or quantified is hydrogen peroxide, the presence of hydrogen peroxide can be confirmed or quantified by a known method, such as the method of measurement using a peroxidase reaction, for example. When employing a peroxidase reaction for measurement, it suffices for the peroxidase that is employed to be an enzyme that is capable of confirming or quantifying the presence of hydrogen peroxide. An example is peroxidase derived from horseradish. So long as it can serve as a substrate for the peroxidase employed, it can also be employed as a color-forming agent. When employing peroxidase derived from horseradish, an example is 4-aminoantipyrine: phenol. The reaction for confirming or quantifying the presence of hydrogen peroxide with peroxidase derived from horseradish is as indicated below:

Chem. 2

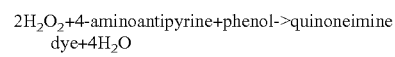

The fluorescent agent or color-forming agent such as 4-aminoantipyrine can be suitably selected based on the type of peroxidase employed.

The hydrogen peroxide that is produced by the L-tryptophan oxidase reaction can be measured using a current detecting type sensor with a hydrogen peroxide electrode. This measurement permits both confirmation and quantification of the presence of hydrogen peroxide. For example, the hydrogen peroxide electrode can be a sensor such as ferrocene, which can be present in carbon paste and a membrane, on which peroxidase and bovine serum albumin have been immobilized with glutaraldehyde as an electrode.

When the product that is used to confirm or quantify is ammonia, measurement can be conducted with an ammonia-detecting reagent. An example of an ammonia-detecting reagent is the indophenol method, which is based on a combination of phenol and hypochlorous acid. Specifically, the sample is mixed with a phenol nitroprus side solution and a perchloric acid solution to produce color, permitting confirmation. The absorbance at 635 nm of the color generated can also be measured to quantify the ammonia.

When the product that is used to confirm or quantify is a deamination product of L-tryptophan in the form of indole pyruvic acid, 2-oxo-acid reductase can be employed to confirm or quantify the presence of indole pyruvic acid.

<The Kit for Analyzing L-Tryptophan>

The present invention includes a kit for analyzing L-tryptophan can include the following reagents:

L-Tryptophan Oxidase

The L-tryptophan oxidase is identical to that described for the above method of quantifying L-tryptophan. Confirmation and quantification of the presence of L-tryptophan are included in the analysis of L-tryptophan.

The L-tryptophan oxidase can also be a mixture of L-tryptophan oxidase with a stabilizing agent. The stabilizing agent can be glycerol, sucrose, sorbitol, and/or trehalose. The stabilizing agent can be glycerol due to its good stabilizing effect on enzymes.

The kit can further include a reaction buffer, a reagent for detecting hydrogen peroxide, an ammonia-detecting reagent, and/or an indole pyruvic acid-detecting reagent.

The reaction buffer can be used to maintain the reaction solution at a pH suited to the quantification reaction or the like. The L-tryptophan oxidase indicated in the Examples further below has an optimal pH ranging from 8 to 9, so a buffer solution having a pH falling within this range is exemplary.

The reagent for detecting hydrogen peroxide is employed when detecting hydrogen peroxide by fluorescence or color formation, for example. Examples of the reagent for detecting hydrogen peroxide are a combination of the color-forming agent of peroxidase and its substrate. A specific example is a combination of horseradish peroxidase, 4-aminoantipyrine, and phenol.

An example of the ammonia-detecting reagent is the indophenol method based on combining phenol and hypochlorous acid.

An example of the indole pyruvic acid-detecting reagent is the use of 2-oxo-acid reductase.

<The Composition for Analyzing L-Tryptophan>

The present invention includes a composition for analyzing L-tryptophan containing L-tryptophan oxidase. The L-tryptophan oxidase in this composition is identical to the L-tryptophan oxidase described for the above method for quantifying L-tryptophan. The analysis of L-tryptophan includes confirmation and quantification of the presence of L-tryptophan. The composition for analysis can contain, by way of example, an agent for stabilizing the enzyme, a buffer solution, and a buffering agent in addition to L-tryptophan.

The agent for stabilizing L-tryptophan oxidase can be glycerol, sucrose, sorbitol, and/or trehalose. The stabilizing agent can be glycerol due to its good stabilizing effect on enzymes.

The mixing ratio of enzyme and stabilizing agent can be, for example, 10 to 70 mass parts of stabilizing agent per 100 mass parts of enzyme from the perspective of permitting the stable storage of the enzyme for extended periods. The quantity of stabilizing agent can fall within a range of 20 to 60 mass parts, or within a range of 30 to 50 mass parts, per 100 mass parts of enzyme.

<The Enzyme Sensor>

The present inventor includes an enzyme sensor for detecting or quantifying L-tryptophan with L-tryptophan oxidase. The L-tryptophan oxidase employed in the enzyme sensor is identical to that described for the above method for quantifying L-tryptophan.

The detection electrode is an electrode for detecting hydrogen peroxide. The electrode for detecting hydrogen peroxide can be an enzymatic hydrogen peroxide electrode or a membrane hydrogen peroxide electrode. When L-tryptophan oxidase reacts with L-tryptophan, it produces hydrogen peroxide. Thus, the hydrogen peroxide can be detected with a hydrogen peroxide-detecting electrode. An example of an enzymatic hydrogen peroxide electrode is a sensor such as ferrocene which is present in a carbon paste and a membrane, on which peroxidase and bovine serum albumin have been immobilized with glutaraldehyde as an electrode. The membrane hydrogen peroxide electrode is an electrode of a type in which a membrane separates the hydrogen peroxide from the electrode with which it reacts.

From the perspective of conducting the detection or quantification of the L-tryptophan at a higher level of precision, the above L-tryptophan oxidase can be disposed on the surface of the detection electrode or in the vicinity of the detection electrode. When disposed on the surface of the detection electrode, it can be immobilized on the surface of the detection electrode or not. Immobilization on the surface of the detection electrode affords the advantage of permitting repeat use of the sensor of the present invention. Furthermore, the L-tryptophan oxidase can be disposed together with the above enzyme stabilizing agent on the surface of the detection electrode or in the vicinity of the detection electrode. The stabilizing agent can be glycerol, sucrose, sorbitol, and/or trehalose.

EXAMPLES

The present invention is described more specifically below through Examples. However, the present invention is not limited to the Examples.

1. Example of Preparation of L-Tryptophan Oxidase

Genomic DNA of *Chromobacterium violaceum* NBRC 12614 was prepared. Employing it as template, PCR was conducted with the primers of SEQ ID NOS: 5 and 6 that had been designed based on the sequence (AF172851.1) of the individual bacterium in the base sequence database. The L-tryptophan oxidase gene vioA was thus amplified. The amplification product was inserted into pET-28a to obtain a plasmid for expressing vioA. A fragment of a cosmid pTYMCsta (Onaka, H., Taniguchi, S., Igarashi, Y., and Furumai, T. (2002) J Antibiot 55, 1063-1071) containing a fragment of the genome of *Streptomyces* sp. TA-A0724 that had been treated with StuI was inserted into a vector pTYM19 (Onaka, H., Taniguchi, S., Ikeda, H., Igarashi, Y., and Furumai, T. (2003) J Antibiot 56, 950-956) that had been treated with HincII, and the L-tryptophan oxidase gene StaO was subcloned. Employing a QuikChange site-directed mutagenesis kit made by Strategene and the primers of SEQ ID NOS: 7 to 10, the sequence of the above subcloned plasmid was changed. The StaO gene was cut from this plasmid by treatment with NdeI and HindIII, and inserted into pET-26b that had been treated with the same restriction enzymes to obtain an StaO expression plasmid. The primers were designed so that a His-tag was added to the N or C end of each enzyme. *E. coli* BL21 (DE3) strain was transformed with each of the expression plasmids to obtain VioA or StaO heterogeneous expression strains. The base sequences of the primers were as follows.

```
VioA-F:
                                          (SEQ ID NO: 5)
ATTCTAGACATATGAAGCATTCTTCCGATATCTG

VioA-R:
                                          (SEQ ID NO: 6)
AATAAGCTTCGCGGCGATGCGCTG
```

-continued

StaO-N-sense:
(SEQ ID NO: 7)
TACTGGAGGAAACATATGACGGCACCC

StaO-N-anti:
(SEQ ID NO: 8)
CAAGGGTGCCGTCATATGTTTCCTCCA

StaO-C-sense:
(SEQ ID NO: 9)
GACCGGTCGGCGAAGCTTTCTTCGACCTG

StaO-C-anti:
(SEQ ID NO: 10)
GCAGGTCGAAGAAAGCTTCGCCGACCGGT

The various heterogeneous expression strains were cultured by shaking at 37° C. until the OD600 reached 0.6 to 0.8. At that point, IPTG was added to a final concentration of 0.5 mM to induce expression. Culturing was conducted for 16 hours at 16° C. following the induction of expression, and the target enzyme was obtained in the soluble fraction. The yield of StaO was further enhanced by coexpression of the chaperone plasmid pG-KJE8 made by Takara.

The supernatant of each solution of the ruptured expression strains was loaded onto an Ni Sepharose column made by GE Healthcare, washed with 20 mM Tris-HCl and 50 mM imidazole (pH 8.0), and then eluted with a solution of 20 mM Tris-HCl and 500 mM imidazole (pH 8.0) to purify and recover the target enzyme. The base sequences of these enzymes were determined, and are shown as SEQ ID NOS: 3 and 4. The amino acid sequences of the enzymes are shown as SEQ ID NOS: 1 and 2.

2. An Example of the L-Tryptophan Oxidase Activity Measurement Conditions

A reaction solution of 20 mM tris-hydrochloric acid buffer (pH 8.0), 5 mM L-tryptophan, 1 mM phenol, 1 mM 4-aminoantipyrine, 15 U/mL horseradish-derived peroxidase, and some quantity of L-tryptophan oxidase enzyme solution was prepared and the change in absorbance at 505 nm was measured at 30° C. The mol absorbance coefficient of quinoneimine dye was considered to be 6.4 mM$^{-1}$·cm$^{-1}$. Activity generating 1 μmol of hydrogen peroxide per minute was defined as 1 U. The detection limit of this method was 0.5%.

3. The Dependence of Activity on pH

Potassium phosphate buffers (pH 6.5, 7.0, 7.5, 8.0, 8.5) and tris-hydrochloric acid buffers (pH 8.0, 8.5, 9.0) were employed as buffers and the activity of StaO when each buffer was employed was measured. Reaction solutions each containing 20 mM of one of the above buffers, 5 mM of L-tryptophan, 1 mM of phenol, 1 mM of 4-aminoantipyrine, 15 U/mL of horseradish-derived peroxidase, and StaO enzyme solution were prepared and the change in absorbance at 505 nm was measured at 30° C. As a result, StaO exhibited maximal enzymatic activity at pH 8.0 to 9.0. The optimal pH for VioA has been reported in Balibar, C. J., and Walsh, C. T. (2006) Biochemistry 45, 15444-15457 to be 9.25.

4. The Substrate Specificity for Amino Acids of L-Tryptophan Oxidase

Reaction solutions each containing 20 mM of tris-hydrochloric acid buffer (pH 8.0), 1 mM of phenol, 1 mM of 4-aminoantipyrine, 15 U/mL of horseradish-derived peroxidase, 0.2 to 20 mU/mL of L-tryptophan oxidase, and 0.5 mM of an amino acid (one of the 20 protein-constituting amino acids) were prepared and the change in absorbance at 505 nm was measured at 30° C. The relative activity for each amino acid was calculated from the measurement values obtained, yielding the results given in Table 1. The detection limit of this method was 0.5%.

StaO did not exhibit reactivity to amino acids other than L-tryptophan (the relative activity was below the detection limit). With respect to L-phenylalanine alone, an extremely low relative activity of 0.5 to 1% of that of L-tryptophan was detected. No reactivity to amino acids other than L-tryptophan was detected for VioA (the relative activity was below the detection limit). As set forth above, both StaO and VioA exhibited extremely high substrate specificity for L-tryptophan.

5. The Km Value of L-Tryptophan Oxidase for L-Tryptophan

Reaction solutions each having 20 mM of tris-hydrochloric acid buffer (pH 8.0), 1 mM of phenol, 1 mM of 4-aminoantipyrine, 15 U/mL of horseradish-derived peroxidase, 0.5 mU/mL of L-tryptophan oxidase, and 0, 6.3, 13, 25, 50, 100, or 500 μM of L-tryptophan were prepared and the change in absorbance at 505 nm was measured at 30° C.

The StaO activity that was calculated at each L-tryptophan concentration is given in FIG. 1. Based on this result, the Km value of StaO for L-tryptophan was calculated to be 19 μM. Further, the Km value of VioA is reported to be 30 μM (Balibar, C. J., and Walsh, C. T. (2006) Biochemistry 45, 15444-15457). These values are much lower than the value (650 μM) for L-amino acid oxidase derived from *Coprinus* sp., and equivalent or lower than the Km values for the substrates of enzymes that are generally used to quantify amino acids. This showed that, StaO and VioA had good properties as quantifying enzymes even in samples with low concentrations of L-tryptophan.

TABLE 1

The relative activity and Km values of StaO, VioA, and enzymes employed in background art for various amino acids

|  |  | StaO | VioA | Coprinus-derived L-amino acid oxidase (Patent Reference A) |
|---|---|---|---|---|
| Relative activity | L-tryptophan | 100% | 100% | 100% |
|  | L-phenylalanine | 1%*[2] | No activity*[3] | 7% |
|  | L-tyrosine | No activity | No activity | 3% |
|  | Other amino acids*[1] | No activity | No activity | No activity or unreported |
| Km value for L-tryptophan |  | 19 μM | 30 μM | 650 μM |
| Molecular weight of subunit |  | 55.6 kDa | 46.7 kDa | 68 kDa |

*[1]L-alanine, L-cysteine, L-aspartic acid, L-glutamic acid, L-glycine, L-histidine, L-isoleucine, L-lysine, L-leucine, L-methionine, L-asparagine, L-proline, L-glutamine, L-arginine, L-serine, L-threonine, and L-valine.
*[2]The relative activity for L-phenylalanine is the average value for three measurements. The detection limit in this measurement was 0.5%, and the quantification limit was 1.5%.
*[3]"No activity" means at or below the detection limit. The detection limit was 0.5%.

6. Preparation of an L-Tryptophan Calibration Curve

A reaction solution of 40 mM of tris-hydrochloric acid buffer (pH 8.0), 2 mM of phenol, 2 mM of 4-aminoantipyrine, 30 U/mL of horseradish-derived peroxidase, and 20 mU/mL of L-tryptophan oxidase enzyme solution was prepared. This was mixed with aqueous solutions of 0, 20, 40, 60, 80, and 100 μM of L-tryptophan in an equivalent amount to obtain standard samples. Reactions were conducted at 30° C., the change over time in the absorbance at 505 nm was measured at 30° C., and the progress of the reactions was monitored.

FIGS. 2 to 5 show the measurement results for the samples prepared as set forth above. For both StaO and VioA, a good linear relation was observed between the concentration and absorbance of L-tryptophan at the latest at 20 minutes or later from the start of the reaction, indicating that a calibration curve could be prepared for this reaction system. For the StaO samples in particular, change was exhibited such that the rise in absorbance nearly stopped even when the reaction time was made excessively long. This property can be said to be suitable for a quantification enzyme for which error tends not to occur even when there is variation in the reaction time.

7. Quantification of L-Tryptophan in Human Plasma Samples 7-1. Pretreatment of Human Plasma Samples Human plasma samples were purchased from KOHJIN BIO. Three specimens that had been stored at −20° C. were employed. They were thawed immediately prior to use, and employed as is or following treatment to remove protein by ultrafiltration with a Microcon YM-10 in the L-tryptophan quantification set forth below.

7-2. Quantification of L-Tryptophan in Human Plasma Samples by Instrumental Analysis Quantification was conducted by the precolumn derivatization method employing an ultra-high-speed amino acid analysis system as a comparison for quantification by the enzymatic method. As set forth above, human plasma samples that had been processed to remove protein were fed into an ultra-high-speed amino acid analysis system, the Waters UPLC Amino Acid Analysis Solution System. The procedures in the instruction manual of the system were followed in the derivatization and analysis of the samples. A calibration curve was prepared using standard samples in the form of 0, 20, 40, 60, 80, and 100 μM aqueous solutions of L-tryptophan, and the L-tryptophan in the human plasma samples was quantified.

7-3. Quantification of L-Tryptophan in Human Plasma Samples with L-Tryptophan Oxidase A reaction solution of 40 mM of tris-hydrochloric acid buffer (pH 8.0), 2 mM of phenol, 2 mM of 4-aminoantipyrine, 30 U/mL of horseradish-derived peroxidase, and 20 mU/mL of L-tryptophan oxidase enzyme solution was prepared. To this were admixed equal quantities of 0, 20, 40, 60, 80, and 100 μM L-tryptophan aqueous solutions or human plasma samples before and after deproteinization treatment. Reactions were conducted at 30° C., and the absorbance at 505 nm was measured after 30 minutes. A calibration curve was prepared from the measurement values of the L-tryptophan aqueous solution samples and the L-tryptophan in the plasma samples was quantified.

Figure 6:
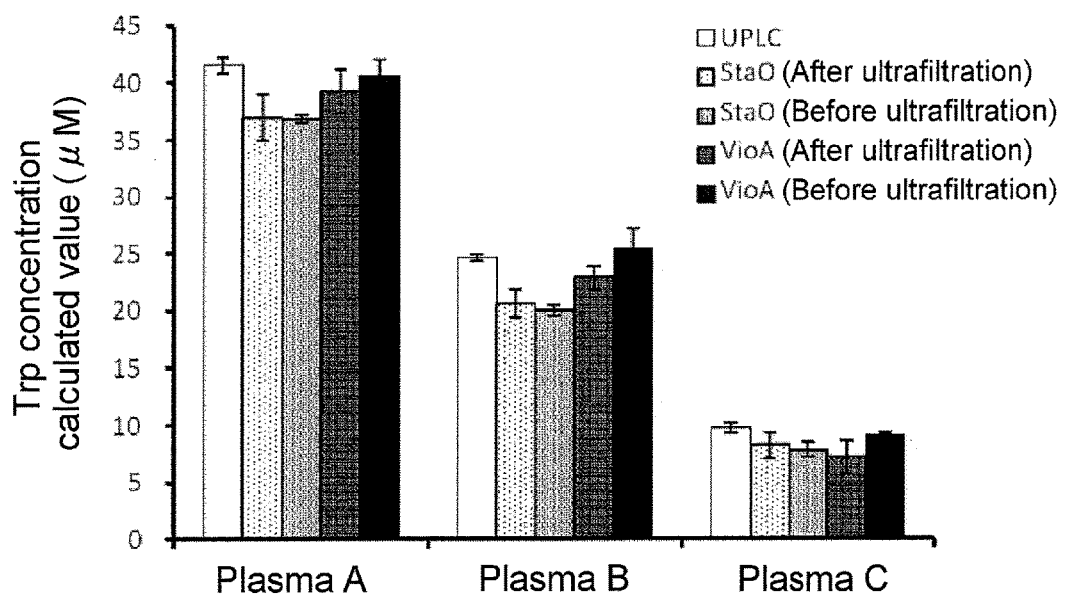
FIG. 6 shows the results of L-tryptophan quantification in human plasma samples by instrumental analysis or with L-tryptophan oxidase.

7-4. A Comparison of Quantification Results for Human Plasma Samples by Instrumental Analysis and L-Tryptophan Oxidase The results of the above measurement are given in FIG. 6. In the quantification systems in which either the enzyme StaO or VioA was employed, values close to the measurement values obtained by instrumental analysis were obtained. This underscored the effectiveness of the quantification method based on L-tryptophan oxidase on human plasma samples.

In the analysis of biological samples by common enzymatic methods, there are numerous cases where quantification properties are lost when a deproteinization treatment is not conducted. In such cases, deproteinization treatment becomes necessary as a pretreatment of the biological sample. However, neither StaO nor VioA was observed to have been quantitatively affected, even in samples that had not been subjected to deproteinization treatment. Thus, the pretreatment of samples was unnecessary in the quantification method with the above enzyme, and it was found to be a particularly convenient and accurate quantification method as an enzymatic method.

8. Stability

Figure 7:
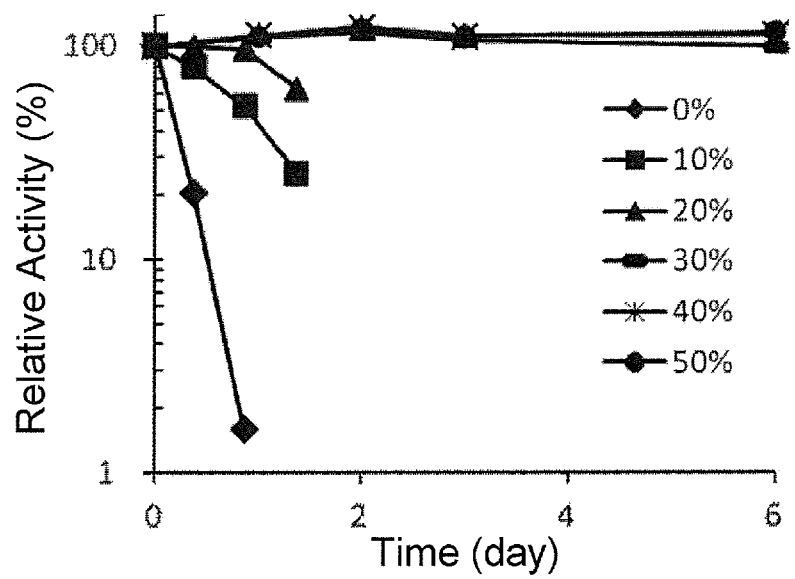
FIG. 7 shows the change over time in StaO residual activity in the presence of various glycerol concentrations.
Figure 8:
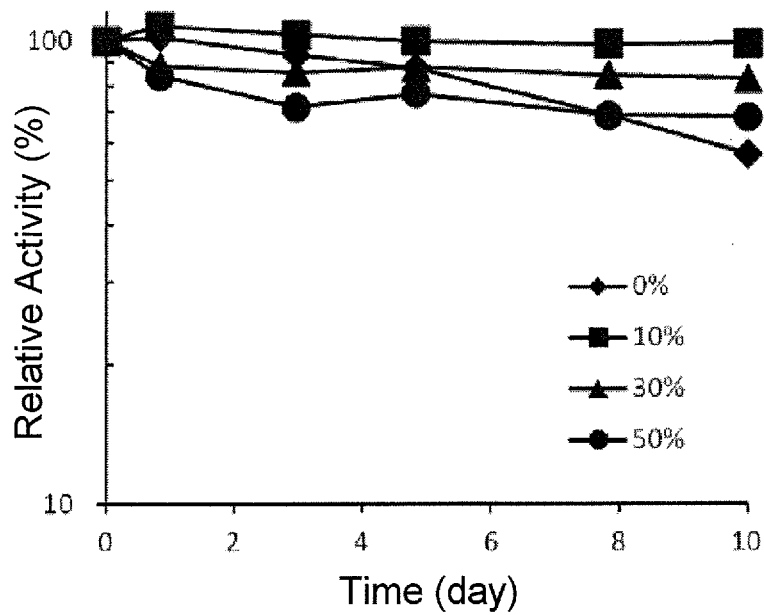
FIG. 8 shows the change over time in VioA residual activity in the presence of various glycerol concentrations.

Glycerol was added to final concentrations of 0 to 50% (v/v) to StaO and VioA purified enzyme solutions. The enzymatic solutions were stored at 4° C., sampled over time, and the activity was measured. The change over time in the residual activity of StaO and VioA stored in the presence of various glycerol concentrations are given in FIGS. 7 and 8. Although StaO was unstable in a solution containing just buffer, it exhibited high stability under conditions were 30% or more of glycerol was added. VioA was relatively stable even without the addition of glycerol, but increased in stability with the addition of 10% or more of glycerol.

Figure 9:
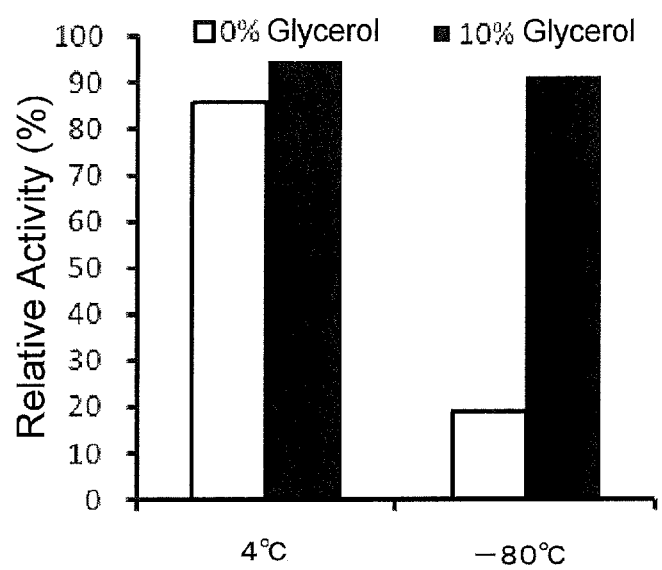
FIG. 9 shows the residual activity following overnight storage of VioA at 4° C. and −80° C. with and without the presence of 10% glycerol.

Glycerol was added to a final concentration of 0 or 10% (v/v) to a VioA purified enzyme solution. The various enzyme solutions were stored overnight at 4° C. or −80° C. and then subjected to activity measurement. FIG. 9 shows the residual activity of VioA enzyme solutions in which 10% glycerol or no glycerol was present. VioA exhibited loss of activity when thawed following freezing, but no such deactivation was observed when 10% glycerol was added.

As set forth above, when 30% of glycerol was added to StaO and no glycerol (10% of glycerol when freezing and thawing were conducted) was added to VioA, they could be employed as stable enzyme solutions.

9. Dependence on Reaction Temperature

StaO and VioA activity measurement was conducted at reaction temperatures of 20, 30, 40, 50, and 60° C. An activity measurement reaction solution of 20 mM of tris-hydrochloric acid buffer (pH 8.0), 1 mM of L-tryptophan, 1 mM of phenol, 1 mM of 4-aminoantipyrine, 15 U/mL of horseradish-derived peroxidase, and L-tryptophan oxidase enzyme solution was employed. Everything in the above reaction solution but the peroxidase and L-tryptophan oxidase enzyme solution was admixed, and 10 minutes of preincubation was conducted at various temperatures. While maintaining the temperature of the reaction solution, the peroxidase and the L-tryptophan oxidase enzyme solution were added and the reaction was begun. The change in absorbance at 505 nm was rapidly measured. Table 2 shows the relative activity values for StaO and VioA at various temperatures as calculated from the measurement results. Both enzymes exhibited a rise in activity with the rise in the reaction temperature. The effect of deactivation at high temperature became marked in StaO at 60° C. and in VioA at 50° C. and above, making it difficult to accurately measure the activity.

TABLE 2

Relative activity at various reaction temperatures with the activity at 20° C. as 100

| | StaO | VioA |
|---|---|---|
| 20° C. | 100 | 100 |
| 30° C. | 156 | 197 |
| 40° C. | 268 | 327 |
| 50° C. | 427 | 327* |
| 60° C. | 480* | —** |

*The estimated value when greatly impacted by thermal deactivation
**Measurement precluded by acute thermal deactivation 10. Thermal Stability The activity was measured after heat treating StaO enzyme solutions containing 20% glycerol and VioA enzyme solutions containing 10% glycerol for 1 hour at 30, 40, 50, 60, and 70° C. Table 3 shows the residual activity of each enzyme solution following the heat treatment. Each of the enzymes exhibited pronounced thermal deactivation at heat treatments of 40° C. and higher. At heat treatments of 50° C. and above, the residual activity dropped below the detection limit.

TABLE 3

Relative activity following heat treatment at various reaction temperatures with activity prior to heat treatment as 100

|  | StaO | VioA |
|---|---|---|
| 30° C. | 73 | 95 |
| 40° C. | 1 | 7 |
| ≥50° C. | <1 | <1 |

INDUSTRIAL APPLICABILITY

L-tryptophan is an essential amino acid. When extremely depleted, the symptom of the lack of niacin is known as the endemic disease pellagra. In the case of excessive intake, the possibility of causing an increase in eosinophils and myalgia syndrome has been pointed out. Thus, the quantification of L-tryptophan is conceivable in food analysis, the quality control of pharmaceuticals and supplements, blood test when symptoms of excess or depletion are exhibited, and enzymatic sensors. Since it is a starting material for substances having important functions within the body, such as in metabolic pathways, niacin, and NAD, even in disease diagnosis "amino indexes" based on aminograms, it can be employed as a numerical value constituting the biomarkers of various diseases. For these reasons, the measurement of the quantity of L-tryptophan in foods, biological samples, and the like can be considered an important technology both industrially and medically. Currently, it has only been practically applied in methods requiring extremely expensive equipment and reagents, such as high performance liquid chromatography. Accordingly, the present invention permits the development of products in the form of L-tryptophan quantification kits, enzymatic sensors, and the like, and can be industrialized as an inexpensive and convenient L-tryptophan quantification method.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for analyzing L-tryptophan in a specimen that contains L-tryptophan and L-phenylalanine, comprising the steps of:
   (A) mixing the specimen, an L-tryptophan oxidase, and water, producing a reaction solution,
   (B) allowing the reaction solution to stand for a prescribed period in the presence of oxygen, producing at least one type of reaction product; and either
   (C) confirming the presence of the at least one type of reaction product due to the action of the L-tryptophan oxidase present in the reaction solution after standing for the prescribed period, or
   (D) measuring the quantity of the at least one type of the reaction product;
   wherein the L-tryptophan oxidase has the amino acid sequence of SEQ ID NO: 1.

2. The method according to claim 1, wherein, prior to step (A), the L-tryptophan oxidase is stored in the presence of a stabilizing agent.

3. The method according to claim 2, wherein the stabilizing agent is selected from the group consisting of glycerol, sucrose, sorbitol, trehalose, and combinations thereof.

4. The method according to claim 1, wherein the reaction product is hydrogen peroxide.

5. The method according to claim 1, wherein the specimen further comprises L-tyrosine.

6. The method according to claim 1, wherein the specimen is human plasma.

7. The method according to claim 5, wherein the specimen is human plasma.

* * * * *

SEQUENCE LISTING

```
<160> NUMBER OF SEQ ID NOS: 10

<210> SEQ ID NO 1
<211> LENGTH: 418
<212> TYPE: PRT
<213> ORGANISM: Chromobacterium violaceum

<400> SEQUENCE: 1

Met Lys His Ser Ser Asp Ile Cys Ile Val Gly Ala Gly Ile Ser Gly
1               5                   10                  15

Leu Thr Cys Ala Ser His Leu Leu Asp Ser Pro Ala Cys Arg Gly Leu
            20                  25                  30

Ser Leu Arg Ile Phe Asp Met Gln Gln Glu Ala Gly Gly Arg Ile Arg
        35                  40                  45

Ser Lys Met Leu Asp Gly Lys Ala Ser Ile Glu Leu Gly Ala Gly Arg
    50                  55                  60

Tyr Ser Pro Gln Leu His Pro His Phe Gln Ser Ala Met Gln His Tyr
65                  70                  75                  80

Ser Gln Lys Ser Glu Val Tyr Pro Phe Thr Gln Leu Lys Phe Lys Ser
                85                  90                  95

His Val Gln Gln Lys Leu Lys Arg Ala Met Asn Glu Leu Ser Pro Arg
            100                 105                 110

Leu Lys Glu His Gly Lys Glu Ser Phe Leu Gln Phe Val Ser Arg Tyr
        115                 120                 125

Gln Gly His Asp Ser Ala Val Gly Met Ile Arg Ser Met Gly Tyr Asp
    130                 135                 140

Ala Leu Phe Leu Pro Asp Ile Ser Ala Glu Met Ala Tyr Asp Ile Val
145                 150                 155                 160

Gly Lys His Pro Glu Ile Gln Ser Val Thr Asp Asn Asp Ala Asn Gln
                165                 170                 175

Trp Phe Ala Ala Glu Thr Gly Phe Ala Gly Leu Ile Gln Gly Ile Lys
            180                 185                 190

Ala Lys Val Lys Ala Ala Gly Ala Arg Phe Ser Leu Gly Tyr Arg Leu
```

```
                195                 200                 205
Leu Ser Val Arg Thr Asp Gly Asp Gly Tyr Leu Leu Gln Leu Ala Gly
    210                 215                 220

Asp Asp Gly Trp Lys Leu Glu His Arg Thr Arg His Leu Ile Leu Ala
225                 230                 235                 240

Ile Pro Pro Ser Ala Met Ala Gly Leu Asn Val Asp Phe Pro Glu Ala
                245                 250                 255

Trp Ser Gly Ala Arg Tyr Gly Ser Leu Pro Leu Phe Lys Gly Phe Leu
            260                 265                 270

Thr Tyr Gly Glu Pro Trp Trp Leu Asp Tyr Lys Leu Asp Asp Gln Val
        275                 280                 285

Leu Ile Val Asp Asn Pro Leu Arg Lys Ile Tyr Phe Lys Gly Asp Lys
    290                 295                 300

Tyr Leu Phe Phe Tyr Thr Asp Ser Glu Met Ala Asn Tyr Trp Arg Gly
305                 310                 315                 320

Cys Val Ala Glu Gly Glu Asp Gly Tyr Leu Glu Gln Ile Arg Thr His
                325                 330                 335

Leu Ala Ser Ala Leu Gly Ile Ala Arg Glu Arg Ile Pro Gln Pro Leu
            340                 345                 350

Ala His Val His Lys Tyr Trp Ala His Gly Val Glu Phe Cys Arg Asp
        355                 360                 365

Ser Asp Ile Asp His Pro Ser Ala Leu Ser His Arg Asp Ser Gly Ile
    370                 375                 380

Ile Ala Cys Ser Asp Ala Tyr Thr Glu His Cys Gly Trp Met Glu Gly
385                 390                 395                 400

Gly Leu Leu Ser Ala Arg Glu Ala Ser Arg Leu Leu Leu Gln Arg Ile
                405                 410                 415

Ala Ala

<210> SEQ ID NO 2
<211> LENGTH: 504
<212> TYPE: PRT
<213> ORGANISM: Streptomyces sp. TP-A0274

<400> SEQUENCE: 2

Met Thr Ala Pro Leu Gln Asp Ser Asp Gly Pro Asp Ala Ile Gly
1               5                   10                  15

Gly Pro Lys Gln Val Thr Val Ile Gly Ala Gly Ile Ala Gly Leu Val
                20                  25                  30

Thr Ala Tyr Glu Leu Glu Arg Leu Gly His His Val Gln Ile Ile Glu
            35                  40                  45

Gly Ser Asp Asp Ile Gly Gly Arg Ile His Thr His Arg Phe Ser Gly
        50                  55                  60

Ala Gly Gly Pro Gly Pro Phe Ala Glu Met Gly Ala Met Arg Ile Pro
65                  70                  75                  80

Ala Gly His Arg Leu Thr Met His Tyr Ile Ala Glu Leu Gly Leu Gln
                85                  90                  95

Asn Gln Val Arg Glu Phe Arg Thr Leu Phe Ser Asp Asp Ala Ala Tyr
            100                 105                 110

Leu Pro Ser Ser Ala Gly Tyr Leu Arg Val Arg Glu Ala His Asp Thr
        115                 120                 125

Leu Val Asp Glu Phe Ala Thr Gly Leu Pro Ser Ala His Tyr Arg Gln
    130                 135                 140

Asp Thr Leu Leu Phe Gly Ala Trp Leu Asp Ala Ser Ile Arg Ala Ile
```

Ala Pro Arg Gln Phe Tyr Asp Gly Leu His Asn Asp Ile Gly Val Glu
145                 150                 155                 160

Leu Leu Asn Leu Val Asp Asp Ile Asp Leu Thr Pro Tyr Arg Cys Gly
            165                 170                 175

Thr Ala Arg Asn Arg Ile Asp Leu His Ala Leu Phe Ala Asp His Pro
        180                 185                 190

Arg Val Arg Ala Ser Cys Pro Pro Arg Leu Glu Arg Phe Leu Asp Asp
    195                 200                 205

Val Leu Asp Glu Thr Ser Ser Ile Val Arg Leu Lys Asp Gly Met
225                 230                 235                 240

Asp Glu Leu Pro Arg Arg Leu Ala Ser Arg Ile Arg Gly Lys Ile Ser
                245                 250                 255

Leu Gly Gln Glu Val Thr Gly Ile Asp Val His Asp Asp Thr Val Thr
            260                 265                 270

Leu Thr Val Arg Gln Gly Leu Arg Thr Val Thr Arg Thr Cys Asp Tyr
        275                 280                 285

Val Val Cys Thr Ile Pro Phe Thr Val Leu Arg Thr Leu Arg Leu Thr
    290                 295                 300

Gly Phe Asp Gln Asp Lys Leu Asp Ile Val His Glu Thr Lys Tyr Trp
305                 310                 315                 320

Pro Ala Thr Lys Ile Ala Phe His Cys Arg Glu Pro Phe Trp Glu Lys
                325                 330                 335

Asp Gly Ile Ser Gly Gly Ala Ser Phe Thr Gly Gly His Val Arg Gln
            340                 345                 350

Thr Tyr Tyr Pro Pro Ala Glu Gly Asp Pro Ala Leu Gly Ala Val Leu
        355                 360                 365

Leu Ala Ser Tyr Thr Ile Gly Pro Asp Ala Glu Ala Leu Ala Arg Met
    370                 375                 380

Asp Glu Ala Glu Arg Asp Ala Leu Val Ala Lys Glu Leu Ser Val Met
385                 390                 395                 400

His Pro Glu Leu Arg Arg Pro Gly Met Val Leu Ala Val Ala Gly Arg
                405                 410                 415

Asp Trp Gly Ala Arg Arg Trp Ser Arg Gly Ala Ala Thr Val Arg Trp
            420                 425                 430

Gly Gln Glu Ala Ala Leu Arg Glu Ala Glu Arg Glu Cys Ala Arg
        435                 440                 445

Pro Gln Lys Gly Leu Phe Phe Ala Gly Glu His Cys Ser Ser Lys Pro
    450                 455                 460

Ala Trp Ile Glu Gly Ala Ile Glu Ser Ala Ile Asp Ala Ala His Glu
465                 470                 475                 480

Ile Glu Trp Tyr Glu Pro Arg Ala Ser Arg Val Phe Ala Ala Ser Arg
                485                 490                 495

Leu Ser Arg Ser Asp Arg Ser Ala
            500

<210> SEQ ID NO 3
<211> LENGTH: 1257
<212> TYPE: DNA
<213> ORGANISM: Chromobacterium violaceum

<400> SEQUENCE: 3
atgaagcatt cttccgatat ctgcattgtc ggcgccggca tcagcggcct gacctgcgcc    60
agccatctgc tcgattcgcc cgcttgccgc ggcctgtcgc tgcgcatctt cgacatgcag   120

```
caggaggcgg gcggccgcat ccgctcgaag atgctggatg gcaaggcttc gatagagctg      180 ggcgcgggc gatactcccc gcagctgcac ccgcatttcc agagcgcgat gcagcattac      240
agccagaaga gcgaggtgta tccgttcacc cagttgaaat tcaagagcca tgtccagcag      300
aagctgaagc gggcgatgaa cgagttgtcg cccaggctga agagcatgg caaggaatcc       360 tttctccagt tcgtcagccg ctaccagggc catgacagcg cggtgggcat gatccgctcc      420
atgggctacg acgcgctgtt cctgcccgac atctcggccg agatggccta cgacatcgtc      480
ggcaagcacc cggaaatcca gagcgtgacc gataacgacg ccaaccagtg gttcgcggcg      540
gaaacgggct ttgcgggcct gatccagggc atcaaggcca aggtcaaggc tgccggcgcg      600
cgcttcagcc tgggttaccg gctgctgtcg gtgaggacgg acggcgacgg ctacctgctg      660
caactggccg cgacgacgg ctggaagctg aacaccgga cccgccacct gatcctggcc        720
atccctccgt cggcgatggc cgggctcaat gtcgacttcc ccgaggcgtg gagcggcgcg      780
cgctacggct cgctgccgct gttcaagggt ttcctcacct acggcgagcc ctggtggctg      840
gactacaagc tggacgacca ggtgctgatc gtcgacaacc cgctgcgcaa gatctacttc      900
aagggcgaca gtacctgtt cttctacacc gacagcgaga tggccaatta ctggcgcggc       960
tgcgtggccg aaggcgagga cggctacctg gagcagatcc gcacccatct ggccagcgcg     1020
ctgggcatcg cccgcgagcg cattccccag cccctcgccc atgtgcacaa gtattgggcg     1080
catggcgtgg agttctgccg cgacagcgat atcgaccatc cgtccgcgct cagccaccgc     1140
gacagcggca tcatcgcctg ttcggacgcc tacaccgagc actgcggctg gatggagggc     1200
ggcctgctca gcgcccgcga agccagccgt ctgctgctgc agcgcatcgc cgcgtga       1257

<210> SEQ ID NO 4
<211> LENGTH: 1515
<212> TYPE: DNA
<213> ORGANISM: Streptomyces sp. TP-A0274

<400> SEQUENCE: 4
gtgacggcac ccttgcagga cagtgacggg ccggacgacg ccatcggtgg accgaagcag       60
gtcaccgtca tcggcgccgg tatcgccggc ctggtgacgg cctatgaact ggaacgcctc      120
ggacatcacg tgcagatcat cgaaggcagt gacgacatag cggccgcat tcacacccac       180 cgcttctccg gtgccggtgg gcccggcccg ttcgccgaga tgggggccat gcggatcccc      240
gccggacacc ggctgaccat gcactacatc gccgaactcg gactgcagaa ccaggtacgg      300
gaattccgga cgctgttctc cgacgacgcc gcctatctgc cgagttccgc cggatatctc      360
cgggtgcgcg aggcgcacga cacgctggtc gacgaattcg ccaccggact gccgagcgcg      420
cactaccgcc aggacaccct gttgttcggt gcctggctgg atgccagcat ccgggccatc      480
gccccacgcc agttctacga cggactgcac aacgacatcg tgtcgaact gctgaatctc       540 gtggacgaca tcgatctgac gcccatcgc tgcggcaccg cccgcaacag gatcgatctg       600
cacgccctgt tcgccgacca tccccgtgta cgggcgtcct gcccaccccg gctcgaacgc      660
ttcctcgacg acgtgctgga cgagaccagc tccagcatcg tgcggctcaa ggacggcatg      720
gacgaactgc cccgccggct cgcctcccgt atccggggga agatctccct gggccaggag     780
gtcaccggca tcgacgtgca cgacgacacc gtgaccctga ccgtccgaca gggcctcagg      840
acggtcacca gaacgtgcga ctacgtggtg tgcaccatcc cgttcacggt cctgaggacg      900
ttgcggctca ccggcttcga ccaggacaag ctcgacatcg tccacgagac caagtactgg      960
```

```
ccggcgacga agatcgcctt ccactgccgg gagcccttct gggagaagga cggcatcagc    1020
gggggcgcct ccttcaccgg cggccatgtc cggcagacct actacccgcc cgccgagggc    1080
gaccccgccc tcggcgcggt cctcctcgcc agctacacca tcggcccgga cgccgaggcc    1140
ctggcccgga tggacgaggc cgagcgcgac gccctcgtgg ccaaggaact cagcgtgatg    1200
caccccgagt tgcgcaggcc cggcatggtc ctcgcagtcg cgggccggga ctggggcgcc    1260
cgccgatggt cccggggcgc cgccaccgtc cgctggggcc aggaggccgc cctccgggag    1320
gccgagcgcc gtgagtgcgc acgaccgcag aagggcctgt tcttcgccgg cgagcactgc    1380
tcgtccaagc cggcctggat cgaggggcc atcgagtccg cgatcgacgc cgcgcacgag     1440
atcgagtggt acgagccgcg cgccagccgc gtcttcgccg cctcccgcct cagccgctcg    1500
gaccggtcgg cgtga                                                     1515
```

<210> SEQ ID NO 5
<211> LENGTH: 34
<212> TYPE: DNA
<213> ORGANISM: Artificial Sequence
<220> FEATURE:
<223> OTHER INFORMATION: VioA-F primer

<400> SEQUENCE: 5
attctagaca tatgaagcat tcttccgata tctg                                34

<210> SEQ ID NO 6
<211> LENGTH: 24
<212> TYPE: DNA
<213> ORGANISM: Artificial Sequence
<220> FEATURE:
<223> OTHER INFORMATION: VioA-R primer

<400> SEQUENCE: 6
aataagcttc gcggcgatgc gctg                                           24

<210> SEQ ID NO 7
<211> LENGTH: 27
<212> TYPE: DNA
<213> ORGANISM: Artificial Sequence
<220> FEATURE:
<223> OTHER INFORMATION: StaO-N-sense primer

<400> SEQUENCE: 7
tactggagga aacatatgac ggcaccc                                        27

<210> SEQ ID NO 8
<211> LENGTH: 27
<212> TYPE: DNA
<213> ORGANISM: Artificial Sequence
<220> FEATURE:
<223> OTHER INFORMATION: StaO-N-anti primer

<400> SEQUENCE: 8
caagggtgcc gtcatatgtt cctcca                                         27

<210> SEQ ID NO 9
<211> LENGTH: 29
<212> TYPE: DNA
<213> ORGANISM: Artificial Sequence
<220> FEATURE:
<223> OTHER INFORMATION: StaO-C-sense primer

<400> SEQUENCE: 9
gaccggtcgg cgaagctttc ttcgacctg                                      29

```
<210> SEQ ID NO 10
<211> LENGTH: 29
<212> TYPE: DNA
<213> ORGANISM: Artificial Sequence
<220> FEATURE:
<223> OTHER INFORMATION: StaO-C-anti primer

<400> SEQUENCE: 10
gcaggtcgaa gaaagcttcg ccgaccggt                                    29
```